United States Patent [19]

Chanda et al.

[11] Patent Number: 4,715,899
[45] Date of Patent: Dec. 29, 1987

[54] LIQUID CLEANER CONTAINING INACTIVATED PROTEASE FOR PROTEIN SOILED CONTACT LENSES

[76] Inventors: Subir Chanda, 17 Arlington Dr., Pittsford, N.Y. 14534; Thomas M. Riedhammer, 52 Appian Dr., Rochester, N.Y. 14606; Andrew M. Tometsko, 105 Brooklawn Dr., Rochester, N.Y. 14618

[21] Appl. No.: 599,123

[22] Filed: Apr. 11, 1984
(Under 37 CFR 1.47)

Related U.S. Application Data

[62] Division of Ser. No. 435,851, Oct. 21, 1982, abandoned.

[51] Int. Cl.$^4$ ................................................ B08B 3/08
[52] U.S. Cl. ........................................ 134/26; 134/42; 252/174.12; 252/DIG. 12; 435/184; 435/264
[58] Field of Search ................................ 134/2, 26, 42; 252/174.12, DIG. 12; 435/264, 184, 219

[56] References Cited

U.S. PATENT DOCUMENTS

| | | | |
|---|---|---|---|
| 3,420,810 | 1/1969 | Katsoyannis et al. | 260/112.7 |
| 3,539,451 | 11/1970 | Heinicke | 435/219 |
| 3,910,296 | 10/1975 | Karageozian et al. | 134/2 |
| 4,285,738 | 8/1981 | Ogata | 134/28 |

OTHER PUBLICATIONS

E. R. Stadtman, Allosteric Regulation of Enzyme Activity, Advance in Enzymology, vol. 28, pp. 41-154, J. Wiley & Son, NY (1966).

*Primary Examiner*—Peter A. Hruskoci
*Attorney, Agent, or Firm*—Bernard D. Bogdon

[57] ABSTRACT

Protein soiled contact lenses are conveniently cleaned by the concurrent use of an aqueous solution containing an inactivated sulfhydryl protease and an aqueous mild thio reducing agent. The protease is allosterically inactivated by reaction with sodium tetrathionate.

8 Claims, No Drawings

LIQUID CLEANER CONTAINING INACTIVATED PROTEASE FOR PROTEIN SOILED CONTACT LENSES

BACKGROUND OF THE INVENTION

This application is a division of application Ser. No. 435,851, filed Oct. 21, 1982, now abandoned.

1. Field of the Invention

This invention relates to a method for removing proteinaceous deposits from contact lenses and the inactivated protease used therein.

2. Description of the Prior Art

One of the problems connected with the soft contact lenses is the method of their cleaning. The very property of the hydrophilic soft lenses, which allows them to absorb up to 150% by weight of water, also allows formulations which might otherwise be used for cleaning to be absorbed and even concentrated and later released when the soft contact lens is on the eye. The release may be much slower than the uptake; therefore, the cleaner continues to build up in the lenses. This build-up eventually affects the physical characteristics of the lenses, including dimension, color and the like. This can have the harmful result of damaging or staining the contact lens itself and/or harming the sensitive tissues of the conjunctiva or cornea.

U.S. Pat. No. 3,910,296 to Karageozian and Rudko discloses a method of removing proteinaceous deposits from soft contact lenses by use of an aqueous solution of proteolytic enzyme such as papain. However, because this solution is autodigestive, its effective shelf storage life is only 12 to 24 hours. Therefore, the desired protease, along with enhancer, adjuvants and modifiers, must be prepared in an absolutely dry form tablet which is hermetically sealed and then distributed to the wearer of contact lenses. The ultimate wearer must then prepare the actual aqueous protease solution used to remove protein deposits from the contact lens. Absolute dryness of the tablet at all times is required if autodigestion and decomposition prior to actual use are to be avoided.

SUMMARY OF THE INVENTION

Protein soiled contact lenses are conveniently cleaned by the concurrent use of an aqueous solution containing sulfhydryl protease, allosterically inactivated by sodium tetrathionate, and an aqueous mild thio reducing agent.

DESCRIPTION OF THE PREFERRED EMBODIMENT

The present invention is applicable to all types of contact lenses. Included within the scope of contact lenses are the so-called "hard contact lenses" which are stiff and not readily deformable under pressure from two fingers or from a thumb and finger. The so-called "hard lenses" are typically manufactured from polymers such as polymethylmethacrylate, polysiloxane or cellulose acetate butyrate. These hard lenses are considered to be non-porous, absorbing only slight, if any, of the solution used to clean and/or disinfect the lens. The soft, hydrophilic gel contact lenses readily temporarily deform under presssure and typically absorb 30 or 40 percent water, by weight, although some variants of these polymers have been reported to absorb as much as twice that amount.

Hydrophilic or partially hydrophilic plastic materials have been described for use in making so-called "soft contact" lenses. For example, U.S. Pat. No. 3,503,393 to Seiderman and U.S. Pat. No. 2,976,576 to Wichterle described processes for producing three-dimensional hydrophilic polymers of polyhydroxyethylmethacrylate in aqueous reaction media, having a lightly or sparingly crosslinked polymeric hydrogel structure and having the appearance of elastic, soft, transparent hydrogels. Other soft contact lenses include lenses made out of silicone and other optically suitable flexible materials.

In this era of convenience and economy, individuals wearing contact lenses are particularly interested in the most convenient methods of cleaning their contact lenses at the least possible cost. Hermetically sealed packaging presents a constant threat of seal breakage and subsequent contamination by moisture of the air. Additionally, it is much more expensive to prepare and maintain any product under conditions of absolute dryness than it is to prepare an aqueous solution and the shipping costs for the water contained therein. Finally, it is much more convenient and quicker for the individual consumer to admix two aqueous solutions to obtain the cleaning product than it is to dissolve a dry tablet for the same purpose. Some consumers, because of space and weight constraints of travel, camping and the like, would accept the time and effort to prepare the solution from a dry tablet if the tablet was not sensitive to atmospheric moisture.

Sulfhydryl protease enzymes are known to have active cysteine groups. For instance, in the amino acid sequence of papain acid group 25, cysteine is known to be active. This activity is described as the allosteric control, see E. R. Stadtman, Allosteric Regulation of Enzyme Activity, Advance in Enzymology, vol. 28, pp 41–154, J. Wiley & Son, New York, NY (1966). The allosteric control site contains a thiol (SH) group. This group is affected by metal ions that bind the SH (thiol) group and by oxidizing and alkylating agents that also bind at the SH site. These proteases can be reversibly inactivated by blocking of the allosteric active (thiol) site. The inactivated protease is readily converted back to the active form at room temperature by the removal of the blocking or inactivation group. This controlled, temporary inactivity is different from denaturing of an enzyme wherein the enzyme is permanently converted to an inactive form.

The sulfhydryl enzymes of this invention include both plant derived and microbial derived protease. Illustrative plant proteases include papain, bromelain, ficin, chymopapain B and the like. Illustrative microbial proteases include proteinase, Streptococus and α-amylase, *β-subtilis*.

The method of U.S. Pat. No., 3,420,810, Katsoyannis and Tometsko, offers a convenient method of preparing the inactivated sulfhydryl proteases of this invention. Briefly, in this method, the oxidizing agent, sodium tetrathionate, is used to modify the allosteric active (thiol) site of the protease. As and when two molecules of the sulfhydryl protease are so oxidized, they interreact, forming a disulfide bridge. While linked together by the disulfide bridge, the protease is inactive. Hereinafter it should be specifically understood that "inactive sulfhydryl protease", "inactive papain", "inactive ficin", etc. mean that the enzyme is in an inactive state due to the joining of two molecules of that enzyme by a disulfide bridge at the allosteric active sulfhydryl site.

The protease is then reactivated at will by the use of a mild thiol reducing agent such as cysteine, mercaptoethanol, sodium thiosulfate, ascorbic acid, glutathione (GSH) and mixtures of the above as well as other thiol reducing agents. The mild thio reducing agent is most advantageously used as a diluent aqueous solution which may contain the various buffers, surfactants, salts for tonicity, other modifiers and buffers which are well known in the art.

The inactive enzymes of this invention have several advantages over the corresponding active form. A comparison of the active form of papain and inactive form of papain is illustrative. Active papain which has been tabletted when put into water has a foul odor. It is well known in the art that papain is subject to denaturing. When denatured, papain will deposit as an objectionable film on contact lenses. In contrast, inactive papain is highly stable, water soluble and free of the objectionable odor. The reactivated papain exhibits greater activity.

Using conventional techniques, the inactivated protease is then prepared in aqueous solution form for distribution to the person desiring to remove proteinaceous deposits from contact lenses. The solution may contain buffers, modifiers, such as salt for tonicity, adjuvants and the like as are commonly employed in the contact lens cleaning art. If desired, all or part of the foregoing may be admixed with the mild thio reducing solution.

Alternatively the inactivated protease may be dried and tabletted with the foregoing adjuvants, modifiers, buffers and pharmaceutically acceptable diluents and tabletting lubricants. No special consideration need be given to tablet storage and handling because of atmospheric moisture.

The following examples are included to illustrate the preparation of the components of the present method and the use of the present method but are not to be considered limiting. Unless otherwise specified, all parts are parts by weight and all temperatures are expressed as degrees Centigrade.

EXAMPLE I

Following the method of U.S. Pat. No. 3,420,810, papain is converted to an inactive form. Papain (28 mg; 1 ml) is incubated with 250 mg/50 ml substrate buffer with sodium tetrathionate at neutral pH. The enzyme solution exhibits the rapid loss of enzymatic activity, reaching zero or no activity within five minutes. The inactive enzyme is then dialyzed for 24 hours with 6 liters of water to remove unreacted tetrathionate. The resulting solution is freeze-dried. A powder of tetrathionate treated papain is obtained. A sample of this material is redissolved in 0.9% sodium chloride solution (1 mg/ml). The redissolved solution continue to be enzymatically inactive over the course of a week at room temperature.

The inactivated papain is dissolved in sodium chloride solution (1 mg/ml). To a cuvette containing substrate buffer (1 ml) is added 20 microliter of inactivated papain solution, followed by 50 ml of sodium thiosulfate solution (200 mg/ml). The solution is incubated for five minutes and then the substrate carbobenzoxy lysine p-nitrophenyl ester is added. After incubation of five minutes, spectrophotometer absorbance at 340 nm is observed. There is significant enzymatic activity. No enzymatic activity is observed under the same conditions with the inactivated enzymes stored in the sodium chloride solution.

The activation of the enzyme is repeated with varying concentrations of cysteine. Cysteine effectively activates the inactivated papain (20 ml) in the concentration range of 4.0 to 800 mg/ml of 0.9% sodium chloride solution. Depending upon the cysteine concentration, activation occurs within five to 30 minutes.

Mercaptoethanol also effectively activates the inactivated papain (20 ml) under the foregoing conditions when 1–10% mercaptoethanol (v/v) is used.

To a vessel containing a soiled contact lens in an aqueous cysteine solution is added a few drops of the inactivated papain/sodium chloride solution. The solution is allowed to stand, the enzyme activates and proceeds to degrade the protein deposits on the lens. The amount of time required to completely free the lens of proteinaceous deposits varies from about 10 minutes to about 10 hours, depending on the amount of inactivated papain added. After rinsing with saline solution, the lens is ready for use.

EXAMPLE II

Example I is repeated except that the enzyme is ficin. The inactivated ficin sodium chloride solution is suitable for addition to a vessel containing protein soiled contact lenses and mercaptoethanol to clean the lens.

The reactivated sulfhydryl protease has all the efficiencies as described to by U.S. Pat. No. 3,910,296. Moreover the inactivated sulfhydryl protease is completely storage stable in the presence of water and is simply reactivated by the addition of a few drops of the aqueous inactivated enzyme solution to the activator solution containing the soiled lenses.

The foregoing examples and methods have been described in the foregoing specification for the purpose of illustration and not limitation. Many other modifications and ramifications will naturally suggest themselves to those skilled in the art, based on this disclosure. These are intended to be comprehended as within the scope of this invention.

The embodiments of the invention in which an exclusive property or privilege is claimed are defined as follows:

1. A process for removing proteinaceous deposits on contact lenses comprising the steps of:
   (i) contacting said contact lens with an aqueous solution of a mild thiol reducing agent wherein the aqueous solution is isotonic to the human eye and said thiol reducing agent is selected from group consisting of: cysteine, mercaptoethanol, sodium thiosulfate, ascorbic acid, glutathione and mixtures thereof;
   (ii) admixing with said solution containing said lens an effective amount of an allosterically inactivated sulfhydryl protease, to remove said proteinaceous deposit from said lens, said protease having been inactivated by reaction with sodium tetrathionate; and
   (iii) allowing said lens to remain in the admixture until said proteinaceous deposit is removed.

2. The process of claim 1 wherein the reducing agent is cysteine.

3. The process of claim 1 wherein the reducing agent is mercaptoethanol.

4. The process of claim 1 wherein the reducing agent is sodium thiosulfate.

5. The process of claim 1 wherein the reducing agent is ascorbic acid.

6. The process of claim 1 wherein the reducing agent is glutathione.

7. The process of claim 1 wherein the inactivated sulfhydryl protease is added to the solution as an aqueous solution.

8. The process of claim 1 wherein the inactivated sulfhydryl protease is added to the solution as a tabletted material.

* * * * *